(12) United States Patent
Yang et al.

(10) Patent No.: US 11,940,429 B2
(45) Date of Patent: Mar. 26, 2024

(54) METHODS FOR AUTHENTICATING BOTANICALS USING A MARKER COMPOUND'S RELATED CHROMATOGRAPHIC PROFILE AND MASS SPECTRAL PROFILE JOINTLY

(71) Applicant: Waters Technologies Corporation, Milford, MA (US)

(72) Inventors: Jinchuan Yang, Hopkinton, MA (US); Paul Rainville, Princeton, MA (US)

(73) Assignee: Waters Technologies Corporation, Milford, MA (US)

( * ) Notice: Subject to any disclaimer, the term of this patent is extended or adjusted under 35 U.S.C. 154(b) by 1007 days.

(21) Appl. No.: 16/400,163

(22) Filed: May 1, 2019

(65) Prior Publication Data
US 2019/0339238 A1  Nov. 7, 2019

Related U.S. Application Data

(60) Provisional application No. 62/665,727, filed on May 2, 2018.

(51) Int. Cl.
*G01N 30/86* (2006.01)
*G01J 3/00* (2006.01)
(Continued)

(52) U.S. Cl.
CPC ............ *G01N 30/8675* (2013.01); *G01J 3/00* (2013.01); *G01N 30/72* (2013.01); *G01N 30/74* (2013.01);
(Continued)

(58) Field of Classification Search
CPC .... G01N 30/8675; G01N 30/72; G01N 30/74; G01N 33/0098; G01N 2030/025;
(Continued)

(56) References Cited

U.S. PATENT DOCUMENTS

2006/0228809 A1\* 10/2006 Clarke .................. G01N 33/82
436/173
2009/0179147 A1   7/2009 Milgram et al.
(Continued)

FOREIGN PATENT DOCUMENTS

CN  101071130 A   11/2007
CN  105044241 A \* 11/2015

OTHER PUBLICATIONS

Lau, Ching Ching, "Application of Near-infrared Spectroscopy in the quality control and chemical analysis of Chinese herbal medicines: A thesis . . . ," Mar. 2012, The Hong Kong Polytechnic University, <https://theses.lib.polyu.edu.hk/handle/200/7011>. (Year: 2012).\*

(Continued)

*Primary Examiner* — Jill A Warden
*Assistant Examiner* — Michael Paul Shimek
(74) *Attorney, Agent, or Firm* — Womble Bond Dickinson (US) LLP; Deborah M. Vernon; Ricardo Joseph

(57) ABSTRACT

A method is provided for authenticating a botanical. The method includes identifying at least one marker compound of the botanical. A sample comprising the botanical is injected into a chromatography system that includes a mobile phase delivery module, an autosampler, a chromatography column, a chromatography column manager, and at least one detector. The method also includes extracting a chromatogram of the at least one marker compound and extracting a spectrum at a chromatographic peak retention time of the at least one marker compound. The method also includes quantifying at least one peak of the extracted chromatogram and quantifying at least one band of the extracted spectrum. The quantified at least one peak of the extracted chromatogram and the quantified at least one band
(Continued)

of the extracted spectrum are compared to a set of authentication criteria to determine authenticity of the botanical.

18 Claims, 11 Drawing Sheets

(51) Int. Cl.
| | | |
|---|---|---|
| *G01N 30/02* | (2006.01) | |
| *G01N 30/72* | (2006.01) | |
| *G01N 30/74* | (2006.01) | |
| *G01N 33/00* | (2006.01) | |
| *G01R 33/46* | (2006.01) | |

(52) U.S. Cl.
CPC ......... *G01N 33/0098* (2013.01); *G01R 33/46* (2013.01); *G01N 2030/025* (2013.01); *G01N 2030/027* (2013.01)

(58) Field of Classification Search
CPC ..... G01N 2030/027; G01N 2030/8813; G01N 30/8679; G01N 30/7233; G01J 3/00; G01R 33/46
See application file for complete search history.

(56) References Cited

U.S. PATENT DOCUMENTS

| | | | |
|---|---|---|---|
| 2013/0140452 A1* | 6/2013 | Kamlage | G01N 33/57438 250/281 |
| 2014/0038217 A1 | 2/2014 | Gorenstein et al. | |
| 2016/0054276 A1 | 2/2016 | Song et al. | |
| 2017/0067865 A1 | 3/2017 | Shimomura et al. | |
| 2017/0131248 A1* | 5/2017 | Kageyama | H01J 49/004 |

OTHER PUBLICATIONS

Sumner et. al., "Proposed minimum reporting standards for chemical analysis," Sep. 12, 2007, Metabolomics, Iss. 3, pp. 211-221, DOI:10.1007/s11306-007-0082-2. (Year: 2007).*

Waters Corporation, "Empower Software Acquisition and Processing: Theory Guide," 2002, Waters Corporation, <https://www.researchgate.net/profile/Stephen_Treimer/post/Does_anyone_know_of_a_resource_to_self-learn_Waters_Empower_3_software/>. Direct ALT URL <tinyurl.com/4zyyuv5z>. (Year: 2002).*

Agilent Technologies ("A Guide to Interpreting Detector Specifications for Gas Chromatographs: Technical Note," 2005, Agilent Technologies, <agilent.com/cs/library/technicaloverviews/Public/5989-3423EN.pdf>. (Year: 2005).*

Farag et al., "Comparative metabolite profiling and fingerprinting of medicinal licorice roots using a multiplex approach of GC-MS, LC-MS and 1D NMR techniques," Feb. 13, 2012, Phytochemistry, vol. 76, p. 60-72, DOI:10.1016/j.phytochem.2011.12.010 (Year: 2012).*

Liang et al., "Quality control of herbal medicines," Dec. 5, 2004, Journal of Chromatography B, vol. 812, Iss. 1-2, p. 53-70, DOI:10.1016/j.jchromb.2004.08.041. (Year: 2004).*

Shimadzu, "Shimadzu's Fundamental Guide to Gas Chromatography Mass Spectrometry (GCMS)," Mar. 2020, <https://www.shimadzu.com/an/sites/shimadzu.com.an/files/pim/pim_document_file/others/11555/ico220013.pdf>. (Year: 2020).*

Geng et al. "Feruloyl dopamine-O-hexosides are efficient marker compounds as orthogonal validation for authentication of Black Cohosh (Actaea racemosa)—an UHPLC-HRAM-MS Chemometrics Study." Anal. Bioanal. Chem. 409.10(2017): 2591-2600.

Jiang et al. "Evaluation of the Botanical Authenticity and Phytochemical Profile of Black Cohosh Products by High-Performance Liquid Chromatography with Selected Ion Monitoring Liquid Chromatography-Mass Spectrometry." J. Agric. Food Chem. 54.9(2006): 3242-3253.

Li et al. "Chemical markers for the quality control of herbal medicines: an overview." Chinese Med. 3(2008): 7.

Custers et al. "Chromatographic fingerprinting as a strategy to identify regulated plants in illegal herbal supplements." Talanta. 164(2016): 490-502.

Xie et al. "Chromatographic fingerprint analysis—a rational approach for quality assessment of traditional Chinese herbal medicine." J. Chromatogr. A. 1112(2006): 171-180.

Lau. "Application of Near-Infrared Spectroscopy in the Quality Control and Chemical Analysis of Chinese Herbal Medicines." The Hong Kong Polytechnic University, Department of Appied Biology and Chemical Technology. Doctor of Philosophy thesis, Mar. 2012.

Li et al. "Fast identification of raw medical materials and its capsules using the comparative method of HPLC fingerprint." Chinese Traditional Patent Medicine. 35.1(2013): 143-147. Chinese Original with English machine-translation.

* cited by examiner

| SAMPLE NAME | RT | % AREA | PEAK TYPE PEAK TYPE | MS MATCH 1 SPECT. NAME | EXPECTED MASS 1 (Da) | EXPECTED INTENSITY 1 (%) | EXPECTED MASS 2 (Da) | EXPECTED INTENSITY 2 (%) | EXPECTED MASS 3 (Da) | EXPECTED INTENSITY 3 (%) | EXPECTED MASS 4 (Da) | EXPECTED INTENSITY 4 (%) | EXPECTED MASS 5 (Da) | EXPECTED INTENSITY 5 (%) |
|---|---|---|---|---|---|---|---|---|---|---|---|---|---|---|
| U1 *BLACK COHOSH | 5.773 | *5 | FOUND | BLACK COHOSH#67 | 621.4 | *9 | 643.5 | 10 | | | | | | |
| U2 BLACK COHOSH | 5.750 | 44 | FOUND | BLACK COHOSH#67 | 621.5 | 100 | 643.5 | 50 | 622.5 | 30 | 644.5 | 18 | 603.4 | 20 |
| U3 BLACK COHOSH | 5.771 | 43 | FOUND | BLACK COHOSH#66 | 621.4 | 100 | 643.5 | 68 | 622.5 | 38 | 644.5 | 26 | 603.5 | 21 |
| U4 *BLACK COHOSH | 5.766 | *4 | FOUND | BLACK COHOSH#66 | 621.4 | *49 | 643.5 | 28 | 622.4 | *15 | 644.4 | 10 | | |
| M-5 *BLACK COHOSH | 5.773 | 48 | FOUND | BLACK COHOSH#66 | 621.4 | *31 | 643.5 | 100 | 622.4 | *13 | 644.5 | 28 | 603.5 | *6 |
| M-10 *BLACK COHOSH | 5.774 | 59 | FOUND | BLACK COHOSH#68 | 621.5 | *36 | 643.5 | 100 | 622.4 | *9 | 644.5 | 39 | 603.4 | *6 |

FIG. 6

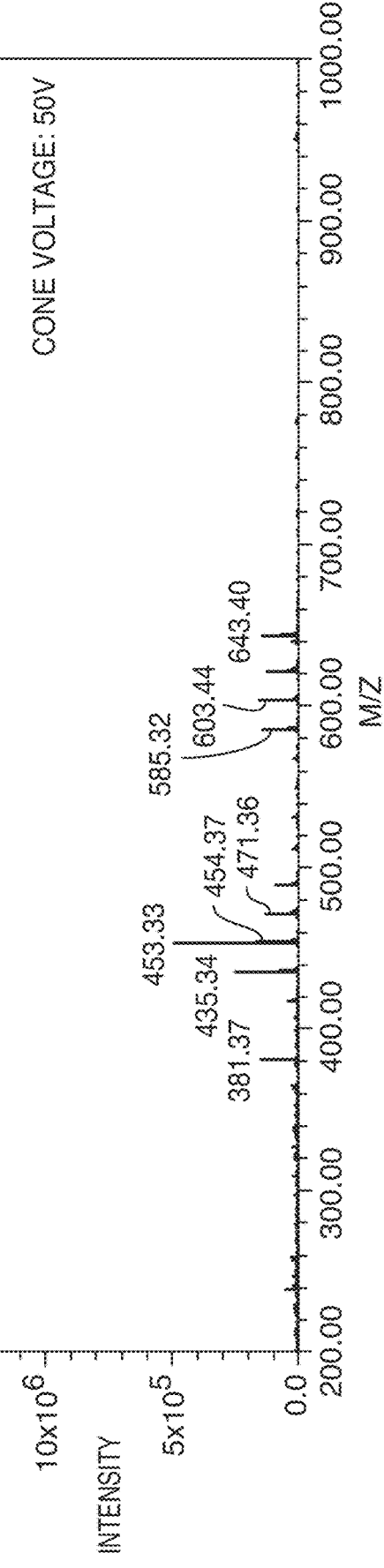
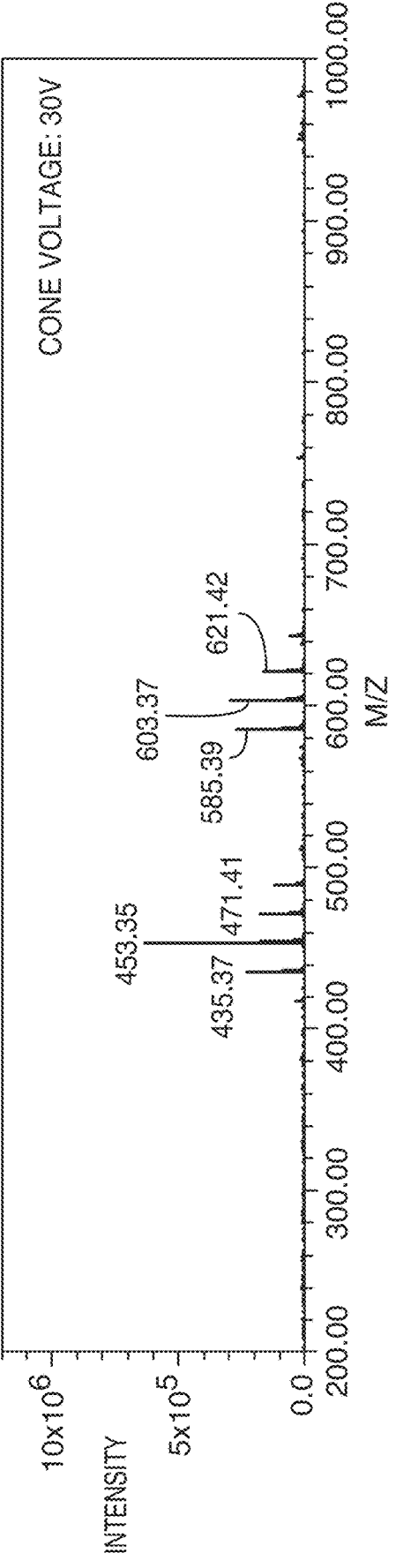
FIG. 7A
FIG. 7B

METHODS FOR AUTHENTICATING BOTANICALS USING A MARKER COMPOUND'S RELATED CHROMATOGRAPHIC PROFILE AND MASS SPECTRAL PROFILE JOINTLY

CROSS REFERENCE TO RELATED APPLICATIONS

This application claims priority to and benefit of U.S. provisional patent application No. 62/665,727 filed on May 2, 2018 entitled Methods for Authenticating Botanicals Using a Marker Compound's Related Chromatographic Profile and Mass Spectral Profile Jointly, the entire contents of which is incorporated herein by reference in its entirety.

FIELD OF THE TECHNOLOGY

The present disclosure relates to methods for authenticating botanicals using a marker compound's related chromatographic profile and mass spectral profile jointly. In particular, the present technology relates to the use of a marker-fingerprint-oriented approach that focuses on one or more markers and uses the marker related chromatographic profiles and the marker related mass spectral profiles for the authentication of botanicals or complex samples.

BACKGROUND

Botanical ingredients are widely used in dietary supplements, herbal medicines, cosmetics and personal care products. Potential contamination or misidentification of plants due to the lack of standardization of production has been a health concern to consumers. Ascertaining the authenticity of botanical ingredients and processed products is a challenging task due to the complex phytochemical constituents, the natural variation in phytochemical profile and the similar phytochemical profile in closely related species. Liquid chromatography (LC) coupled with mass spectrometry (MS) is one of the most effective analytical techniques for the authenticity evaluation. However, LC-MS has not been widely used in routine analytical labs for authenticity testing due to the relatively high cost of mass spectrometers and the high level of expertise needed.

There are generally two techniques that can be used for botanical authentication. One is a marker-oriented approach, the other is a fingerprint-oriented approach. In the marker-oriented approach, one or several compounds are identified as the markers for an authentic botanical. The presence or the concentration levels of these marker compounds are used as the basis for the authenticity evaluations. In the fingerprint-oriented approach, one or several fingerprints of an authentic botanical are collected and used as the reference(s) in the authentication process. The fingerprints can be chromatographic profiles, or spectroscopic profiles, such as UV/Vis, FT-IR, NMR spectra. The fingerprint approach is suitable for complex samples, especially when the key markers, or the key active ingredients, are not well established. Traditional herbal medicines, for example, are often tested by the fingerprint-oriented method for authentication and/or quality control.

Chemometric analysis techniques, such as Principle Component Analysis, Similarity Analysis, Clustering Analysis, are powerful data processing tools that can also be used in the authentication and classification of botanicals. However, the data processing in these techniques are often sophisticated and time consuming.

SUMMARY

What is needed is a less time-consuming and simpler method for analyzing botanicals and other complex compounds that can be performed in routine analytical labs without the use of complicated data processing techniques. The technology includes a combination of the marker-oriented approach and the fingerprint-oriented approach. The technology focuses on one or more (for example, two, three, four, five, etc.) markers and uses the marker related chromatographic profiles and the marker related mass spectral profiles for the authentication of botanicals or complex samples. For example, in the black cohash example below, cimiracemosdie C is used as the target marker and its extracted ion chromatogram profile (at its molecular ion mass to charge ration (m/z)) and its extracted mass spectral profile (at the marker's chromatographic peak position) are used together as the basis for back cohash authentication.

One benefit of the technology is that it is much simpler to process the data as compared to the fingerprint-oriented approach. The fingerprint oriented approach often uses sophisticated data analysis tools, which are time consuming and complicated. In addition, special data processing software is often needed. This is not suitable for routine analytical labs. The technology of the present disclosure, i.e., the marker-fingerprint approach, uses the features of the correlated two dimensional fingerprints of the marker compound(s) to simplify the data process. The data processing is simple, fast, and easy to be implemented in routine analytical labs.

In one aspect, the technology features a method for authenticating a botanical. The method includes identifying at least one marker compound of the botanical. The sample comprising the botanical is injected into a chromatography system that includes a mobile phase delivery module, an autosampler, a chromatography column, a chromatography column manager, and at least one detector. The method also includes extracting a chromatogram of the at least one marker compound and extracting a spectrum at a chromatographic peak retention time of the at least one marker compound. The extracted chromatogram includes at least one peak and the extracted spectrum includes at least one band. The at least one peak of the extracted chromatogram is integrated. The method further includes quantifying the at least one peak of the extracted chromatogram and quantifying the at least one band of the extracted spectrum. The quantified at least one peak of the extracted chromatogram and the quantified at least one band of the extracted spectrum are compared to a set of authentication criteria to determine authenticity of the botanical. The method can include one or more of the following embodiments or features.

In some embodiments, the botanical includes a plant extract, a plant powder, a plant tincture, an herbal medicine, or a botanical ingredient for cosmetic and personal care products. The sample that includes the botanical can have a consistent concentration of about 5 mg/ml. In other embodiments, the sample has a consistent concentration that is appropriate for the detector that is used, for example, about 1 mg/ml, about 2 mg/ml, about 3 mg/ml, about 4 mg/ml, about 6 mg/lm, about 7 mg/ml, about 8 mg/ml, about 9 mg/ml or about 10 mg/ml. A consistent concentration allows for some variation in concentration as the data processing methods can be normalized. However, if the concentration is too low and barely any signal is detected or the concentration is too high resulting in signal truncation, then the concentration needs to be adjusted to an appropriate level (i.e., between the too low and too high scenarios). In general, it is preferable to prepare the samples having the same concentration. Appropriate mass detectors include, but are not limited to ACQUITY® QDa® mass detector (commercially available from Waters Technologies Corporation, Milford, MA), SQ Detector 2 (commercially available from Waters Technologies Corporation, Milford, MA), Xevo® TQD mass detector (commercially available from Waters Technologies Corporation, Milford, MA).

In some embodiments, the chromatography system is a liquid chromatography system, a gas chromatography system, or a supercritical fluid chromatography system.

The detector can be a mass spectrometry analyzer. In some embodiments, the mass spectrometry analyzer is operated in a scan mode. The chromatogram can be extracted at a mass to charge ratio of an ion that is characteristic to the at least one marker compound.

The detector can be a UV-Visual spectrophotometer or a photodiode array detector. The chromatogram can be extracted at a UV-Vis wavelength that is characteristic to the at least one marker compound.

In some embodiments, the detector is a Fourier-transform infrared spectrometer. The chromatogram can be extracted at an IR wavenumber that is characteristic to the at least one marker compound.

In some embodiments, the detector is a nuclear magnetic resonance spectrometer. The chromatogram can be extracted at an NMR chemical shift that is characteristic to the at least one marker compound.

In some embodiments, the spectrum is extracted at an apex of the at least one peak. The extracted spectrum can be baseline subtracted.

In some embodiments, integrating the last one peak of the extracted chromatogram includes detecting a start point and an end point of a baseline of the at least one peak, calculating areas and heights of the at least one peak, and finding apex retention times of the least one peak.

In some embodiments, quantifying peaks on the extracted chromatogram includes calculating a relative peak area of the at least one peak, relative to the sum of the peak areas of all the detected peaks on the extracted chromatogram.

The method can also include identifying a mass to charge ratio of an ion that is characteristic to the at least one marker compound, and calculating an intensity of the least one band. In some embodiments, the method includes identifying a maximum absorption wavelength and calculating an intensity of the least one band. The method can also include identifying a maximum absorption wavenumber and calculating an intensity of the least one band. In some embodiments, the method includes identifying a chemical shift of spectral peaks and calculating an intensity of the at least one band.

The intensity can be a relative ion peak abundance of a most intensive ion peak in the extracted spectrum.

All peaks of the extracted chromatogram can be quantified. All bands of the extracted spectrum can be quantified.

In some embodiments, quantifying the at least one peak of the extracted chromatogram includes quantifying a peak retention time, a peak area, a peak relative area, a peak height, a peak relative height, a peak resolution or a combination thereof. In some embodiments, quantifying the at least one band of the extracted spectrum includes quantifying a mass to charge ratio, an ion intensity, a relative intensity, a relative abundance, an absorbance, a transmittance, a wavelength, a wavenumber, a chemical shift, a signal intensity, or a combination thereof.

The botanical can be authenticated when all values of the quantified at least one peak and the quantified at least one band are within a predetermined threshold value and the extracted spectrum matches a predetermined spectrum.

In some embodiments, at least two marker compounds of the botanical are determined.

In some embodiments, extracting the chromatogram includes extracting chromatograms for each of the at least two marker compounds. In some embodiments, extracting the spectrum comprises extracting spectrum for each of the at least two marker compounds at each of the at least two marker compounds chromatographic peak retention times.

BRIEF DESCRIPTION OF THE FIGURES

FIG. 6 is a screen shot of an Empower® software authenticity test report for commercial and home-made samples, according to an illustrative embodiment of the technology.

FIG. 7A is a mass spectrum showing the effects of cone voltage (50V) on the cimiracemoside C mass spectrum, according to an illustrative embodiment of the technology. The cone voltages are shown in the sepctra.

FIG. 7B is a mass spectrum showing the effects of cone voltage (30V) on the cimiracemoside C mass spectrum, according to an illustrative embodiment of the technology. The cone voltages are shown in the sepctra.

DETAILED DESCRIPTION

The technology includes a combination of the marker-oriented approach and the fingerprint-oriented approach for authenticating a botanical. The botanical to be authenticated can be a plant extract, a plant powder, a plant tincture or an herbal medicine. The botanical can be an ingredient for cosmetic and/or personal care products. The technology focuses on one or more (for example, two, three, four, five, etc.) markers and uses the marker related chromatographic profiles and the marker related mass spectral profiles for the authentication of botanicals or complex samples.

Figure 1:
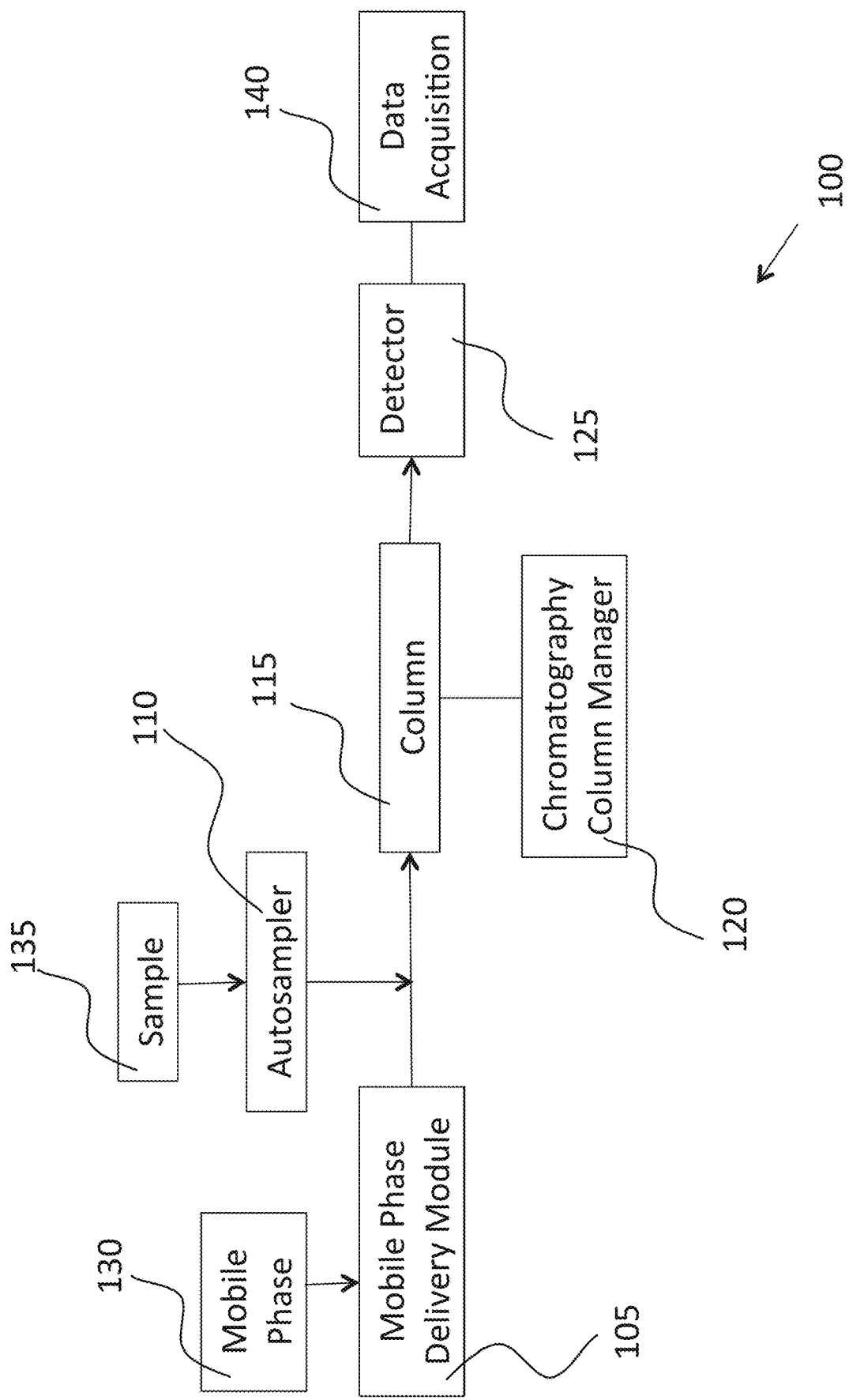
FIG. 1 is a schematic of a chromatography system, according in an illustrative embodiment of the technology.

The method(s) described herein can be used for authenticating a botanical using a chromatography system. FIG. 1 is a schematic of a chromatography system 100 that can be used in the method. The chromatography system includes a mobile phase delivery module 105, an autosampler 110, a chromatography column 115, a chromatography column manager 120, and a detector 125. More than one chromatography column 115 can be included in the chromatography system 100. In some embodiments, the chromatography system includes more than one mobile phase delivery module 105, more than one autosampler 110, more than one chromatography column manager 120, and/or more than one detector 125.

The mobile phase delivery system 105 delivers the mobile phase from a mobile phase reservoir 130 to the chromatography system 100. The autosampler 110 delivers a sample from a sample reservoir 135 into the mobile phase flow stream prior to the combined flow stream entering the chromatography column 115. The chromatography column manager 120 can be used to automatically switch between different columns in the system 100, to heat and cool the column(s) 115, and to track information about each column, for example, which solvents are used in each column to prevent contamination between different solvents. The chromatography column manager 120 is in communication with at least one chromatography column 115.

At least one detector 125, is located downstream of the chromatography column 115. More than one detector or more than one type of detector can be used in the chromatography system 100. The detector can be, for example, a mass spectrometry analyzer, a UV-Visual spectrophotometer, a photodiode array detector, a Fourier-transform infrared spectrometer, a nuclear magnetic resonance spectrometer, or a combination thereof. For examples, in some embodiments, two mass spectrometry analyzers can be used. In other embodiments, a mass spectrometry analyzer and a nuclear magnetic resonance spectrometer can be used. Other combinations of multiple detectors or multiple types of detectors can also be used.

A mass spectrometry analyzer can be operated in a scan mode. In some embodiments, the detector is a single quadrupole mass spectrometer, a tandem quadrupole mass spectrometer, and/or a time of flight mass spectrometer. The ionization mode of the detector can be, for example, an electrospray ionization mode (ESI). Other ionization modes can also be used depending on the specific botanical to be authenticated.

A data acquisition module 140 can be in communication with at least one detector 125. The data acquisition module 140 can used, for example, to gather/collect and analyze data received from the detector 125. The data acquisition module 140 can be a computer having software installed to collect and analyze data, for example to perform integration.

The chromatography system 100 can be any type of chromatography system that is suitable for authenticating a specific botanical as is known to those of skill in the art. For example, the chromatography system 100 can be a liquid chromatography system, a gas chromatography system, or a supercritical fluid chromatography system. Similarly, the chromatography column(s) 115 can be a liquid chromatography column, a gas chromatography column, or a supercritical fluid chromatography column. The mobile phase that is used in the chromatography system 100 can vary depending on the type of chromatography system being used as well as the specific botanical that is being authenticated. One of ordinary skill in the art would understand how to choose a chromatography system and a mobile phase for a botanical to be authenticated. For example, in a supercritical fluid chromatography system, the mobile phase can be carbon dioxide and in a liquid chromatography system the mobile phase can be de-ionized water with formic acid and/or acetonitrile/methanol with formic acid.

Figure 2:
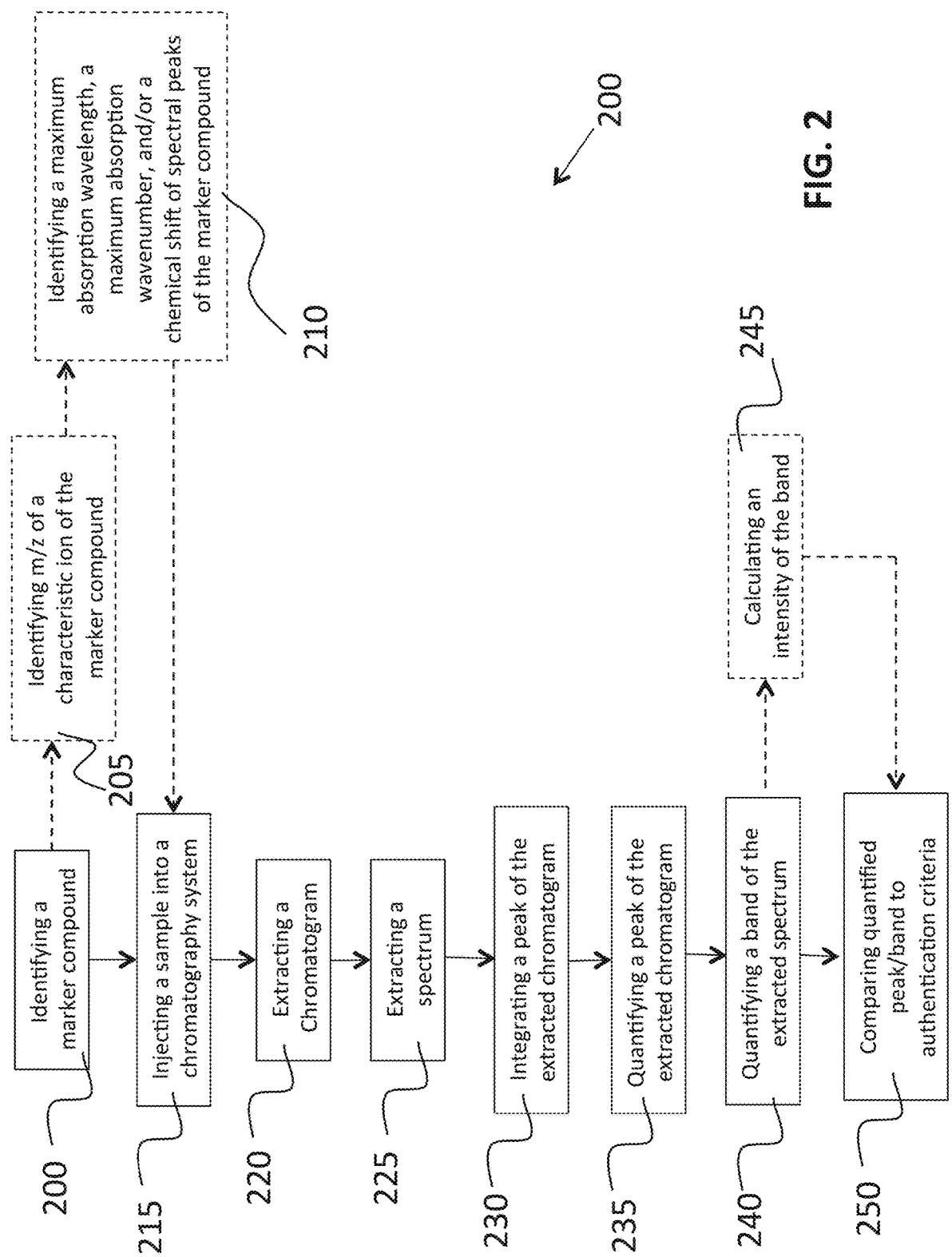
FIG. 2 is a flow chart of a method for authenticating a botanical, according to an illustrative embodiment of the technology.

FIG. 2 is a flow chart 200 showing the method of the present technology. The method for authenticating botanicals uses a chromatography system, for example the chromatography system 100 of FIG. 1. Referring to FIG. 2, the method includes identifying a marker compound 205 of a botanical to be authenticated. The specific marker compound will vary depending on the botanical that is being authenticated. In some embodiments, more than one marker compound, for example, at least two marker compounds, of the botanical to be authenticated can be identified. For example, two, three, four, five, six, seven, or more marker compounds can be identified for any single botanical. The number of marker compounds used, can depend on, for example, the complexity of the authentic botanical as well as the complexity of any known adulterated botanicals. Marker compound(s) can be selected from, for example, the therapeutic components of a botanical or other bioactive, characteristic, main, synergistic, correlative, toxic and/or general components of a botanical. The selection of a marker compound(s) for a botanical is known to those of skill in the art and be done, for example, by using a database of known marker compound(s) for a specific botanical. In some embodiments, candidate marker compounds are selected from the literature, or from exploratory studies of botanicals using high resolution mass spectrometry and chemometric analysis. In certain embodiments, the selected candidate marker can then be further selected or narrowed down to one or a few compounds by comparing the authentic and inauthentic samples chromatograms. Whether one or multiple marker compounds is selected depends on factors, such as, how easily the authentic samples can be differentiated from the inauthentic samples.

Optionally, a mass to charge ratio (m/z) of a characteristic or unique ion of the marker compound can also be identified 205. More than one mass to charge ratio of a characteristic ion of the marker compound can be identified. If multiple marker compounds are used, a mass to charge ratio of at least one characteristic ion of each marker compound can be identified. The mass to charge ratios of characteristic ions of marker compounds are known to those of skill in the art.

The method can also optionally include identifying a maximum absorption wavelength, a maximum absorption wavenumber, and/or a chemical shift or spectral peaks of the at least one marker compound 210.

A sample that includes the botanical is injected 215 into a chromatography system, for example, chromatography system 100 of FIG. 1. The sample can be injected into the chromatography system by being mixed with a mobile phase prior to entering a chromatography column. The sample is separated on the chromatography column and the separated compounds of the sample elute from the chromatography system and enter at least one detector. The concentration of the botanical within the sample can be, for example, about 1 mg/ml to about 10 mg/ml. In some embodiments, the concentration is about 5 mg/ml.

Referring to FIG. 2, a chromatogram of the at least one marker compound is extracted 220. The extracted chromatogram includes at least one peak. When more than one marker compound is used in the method for authenticating a botanical, a chromatogram for each marker compound that is used can be extracted. For example, when two marker compounds are used to authenticate a botanical, two chromatograms can be extracted, one for each of the marker compounds.

Where the chromatogram is extracted depends on the type of detector that is used. If a mass spectrometry analyzer is being used as a detector, the chromatogram is extracted at a mass to charge ratio of an ion that is characteristic to the at least one marker compound. If a UV-Visual spectrophotometer or a photodiode array detector is used, the chromatogram is extracted at a UV-Vis wavelength that is characteristic to the at least one marker compound. If a Fourier-transform infrared spectrometer is used as a detector, the chromatogram is extracted at an IR wavenumber that is characteristic to the at least one marker compound. If a nuclear magnetic resonance spectrometer is used as a detector, the chromatogram is extracted at an NMR chemical shift that is characteristic to the at least one marker compound.

A combination of different types of detectors can be used, for example a mass spectrometry analyzer and a UV-Visual spectrophotometer can both be used. In this example, a chromatogram can be extracted at a mass to charge ratio of an ion that is characteristic to the at least one marker compound and a chromatogram can be extracted at a UV-Vis wavelength that is characteristic to the at least one marker compound. Any combination of detectors can be used that is suitable for authenticating a particular botanical.

In addition, a spectrum at a chromatographic peak retention time of the at least one marker compound is extracted 225. The extracted spectrum includes at least one band. The spectrum can be extracted at an apex of the at least one band. The extracted spectrum can be baseline subtracted. When multiple detectors are used in the chromatography system and/or when multiple marker compounds are used, multiple spectra of the marker compound(s) can be extracted.

In some embodiments, the spectrum is extracted across a RT window that is centered at the peak apex. The RT window can be between a start and an end of a peak integration baseline. The spectrum can be extracted as a combined or average spectra in the RT window.

When more than one marker compound is used in the method for authenticating a botanical, a spectrum for each marker compound can be extracted at each of the marker compounds chromatographic peak retention times. For example, when two marker compounds are used in the method for authenticating a botanical, a spectrum for each of the two marker compounds can be extracted at least of the two marker compounds chromatographic peak retention times.

The at least one peak of the extracted chromatogram is integrated 230. Integrating the last one peak of the extracted chromatogram can include detecting a start point and an end point of a baseline of the at least one peak. The areas and heights of the at least one peak can be calculated and apex retention times of the least one peak can be found. The integration can be done via software stored on, for example, the data acquisition module 140 of the chromatography system 100 of FIG. 1.

Referring back to FIG. 2, the method also includes quantifying the at least one peak of the extracted chromatogram 235 and quantifying the at least one band of the extracted spectrum 240. Quantifying peaks on the extracted chromatogram can include calculating a relative peak area of the at least one peak, relevant to the sum of the peak areas of all the detected peaks on the extracted chromatogram. In some embodiment, quantifying the at least one peak of the extracted chromatogram includes quantifying a peak retention time, a peak area, a peak relative area, a peak height, a peak relative height, a peak resolution or a combination thereof. The peak retention time, peak area, peak relative area, peak height, peak relative height, and peak resolution are all quantifiable properties of the extracted chromatogram. These measured quantifiable properties can be compared to predetermined quantified properties of an authentic botanical to determine whether the sample contains an authentic or adulterated (unauthentic) botanical. For example, a threshold value can be predetermined for each quantifiable property or a subset of quantifiable properties of the extracted chromatogram, and if the measured value is within the limits (e.g., within a certain standard deviation or percentage) of the predetermined value, then the sample contains an authentic botanical. In some embodiments, if the measured quantifiable value is within 1%, 5%, or 10% of the predetermined value then the sample contains an authentic botanical. The determination of the predetermined value, range, or threshold can be based on a statistical analysis of the quantifiable properties of an authentic botanical sample(s). These threshold values can be tested against known unauthentic botanical samples to ensure that the threshold values chosen can accurately distinguish between an authentic and unauthentic botanical sample.

Quantifying the at least one band of the extracted spectrum can include quantifying a mass to charge ratio, an ion intensity, a relative intensity, a relative abundance, an absorbance, a transmittance, a wavelength, a wavenumber, a chemical shift, a signal intensity, or a combination thereof. The mass to charge ratio, ion intensity, relative intensity, relative abundance, absorbance, transmittance, wavelength, wavenumber, chemical shift, and signal intensity are all quantifiable properties of an extracted spectrum. These measured quantifiable properties can be compared to predetermined quantified properties of an authentic botanical to determine whether the sample contains an authentic or adulterated botanical. For example, a threshold value can be predetermined for each quantifiable property or a subset of quantifiable properties of the extracted spectra and if the measured value is within the limits (e.g., within a certain standard deviation or percentage) of the predetermined value, then the sample contains an authentic botanical. In some embodiments, if the measured quantifiable value is within 1%, 5%, or 10% of the predetermined value then the sample contains an authentic botanical. The determination of the predetermined value, range, or threshold can be based on a statistical analysis of the quantifiable properties of authentic botanical samples. These threshold values can be tested against known unauthentic botanical samples to ensure that the threshold values chosen will accurately distinguish between an authentic and unauthentic botanical sample.

In some embodiments, a single peak of the extracted chromatogram and a single band of the extracted spectrum are quantified. In some embodiments, all peaks of the extracted chromatogram and all bands of the extracted spectrum are quantified.

In some embodiments, an intensity of the band(s) of the extracted spectrum is calculated 245. The intensity can be a relative ion peak abundance of a most intensive ion peak (i.e., base ion peak) in the extracted spectrum.

The quantified at least one peak of the extracted chromatogram and the quantified at least one band of the extracted spectrum are compared 250 to a set of authentication criteria to determine authenticity of the botanical. The botanical can be authenticated when all values of the quantified at least one peak and the quantified at least one band are within a predetermined threshold value or range and the extracted spectrum matches a predetermined spectrum. In some embodiments, the predetermined spectrum is part of a spectrum library. The predetermined threshold values can include threshold values for, for example, a mass to charge ratio, an ion intensity, a relative intensity, a relative abundance, an absorbance, a transmittance, a wavelength, a wavenumber, a chemical shift, a signal intensity, a peak retention time, a peak area, a peak relative area, a peak height, a peak relative height, a peak resolution or a combination thereof.

In some embodiments, the method also includes establishing a set of authentication criteria based on an analysis of results of known authentic botanical samples and unauthentic (or adulterated) botanical samples. The authentic botanical samples can represent natural variation of the authentic botanical. The natural variation includes changes in the botanical harvest season and time, geographic location of the harvesting, plant anatomy, and processing and preparation techniques for the authentic sample. The unauthentic (or adulterated) botanical samples can be samples that represent the potential unauthentic or adulterated botanical samples.

When determining the set of authentication criteria based on analyzing the results of authentic botanical samples and unauthentic botanical samples, the order of injection (i.e., the injection order in the sample queue) can be randomized to eliminate possible artifacts related to injection order. The set of authentication criteria can be determined by multiple analyses of authentic botanical samples and unauthentic botanical samples. For example, the set of authentication criteria can be determined based on at least two repeated injections of the authentic botanical samples and at least two repeated injections of the unauthentic botanical samples. In some embodiments, the set of authentication criteria can be determined based on six replicated injections of authentic botanical samples and unauthentic botanical samples.

The authentication criteria are based on quantifiable properties of a chromatogram and a spectrum. Using authentication criteria from a chromatogram and a spectrum of the botanical results in a two dimensional analysis; one dimension from the chromatogram and one dimension from the spectrum.

In some embodiments, the authentication criteria comprises at least one quantifiable property from a chromatogram (e.g., a peak retention time, a peak area, a peak relative area, a peak height, a peak relative height, a peak resolution) and at least one quantifiable property from a spectrum (e.g., mass to charge ratio, an ion intensity, a relative intensity, a relative abundance, an absorbance, a transmittance, a wavelength, a wavenumber, a chemical shift, a signal intensity). In some embodiments, the authentication criteria comprises at least two, at least three, at least four, at least five, or at least six quantifiable properties from a chromatogram and at least two, at least three, at least four, at least five, or at least six quantifiable properties from a spectrum. In some embodiments, the number of quantifiable properties used for the authentication criteria for the chromatogram and spectrum are the same. In other embodiments, the number of quantifiable properties used for the authentication criteria for the chromatogram and spectrum are different. In some embodiments, the authentication criteria comprise all of the quantifiable properties of the chromatogram and all of the quantifiable properties of the spectrum. The specific number and type of quantifiable properties used to authentic a botanical can depend on, for example, the complexity of the botanical to be authenticated.

In some embodiments, only the quantifiable properties of a single chromatographic peak and a single spectral band are used for authentication. In other embodiments, two or more (e.g., two, three, four, five, six, seven, eight, nine, or ten) chromatographic peaks and two or more (e.g., two, three, four, five, six, seven, eight, nine, or ten) spectral bands are used for authentication. In some embodiments, the number of peaks and bands used for authentication is the same and in other embodiments the number of peaks and bands used for authentication is different. In some embodiments, only certain peaks or bands are used for authentication. For example, only the two, three, or four most intensive peaks or bands are used for authentication. An intensive peak can be, for example, a peak with the highest peak area, highest peak relative area, highest peak height, the highest peak relative height, or highest peak resolution. An intensive band can be, for example, a band with the highest ion intensity, the highest relative ion intensity, or the highest relative abundance. The quantifiable property used for intensity can vary depending on the specific botanical to be authenticated.

In some embodiments, the bands used for authentication are the base ion band and the next four most intensive bands. The base ion band and an intensive band can include a molecular ion, a fragment ion, adduct ion(s) and/or isotopic ion(s).

The authentication criteria can also include a spectrum library match, e.g., that the spectrum of the sample containing a botanical, matches a predetermined spectrum of the authentic botanical. The spectrum of authentic botanicals can be stored in a botanical library. The botanical library can be stored on a computer, for example, on data acquisition module 140 of FIG. 1.

The technology described herein uses the correlated two dimensional fingerprints that relate to marker compound(s) to authenticate botanicals. The use of a marker's fingerprint can simplify the data process and allows a simple, fast, and streamlined data process. The method(s) described herein can be implemented in standard chromatography data software and is suitable for routine analytical labs.

The joint use of an extracted ion chromatogram, specific to a marker compound, and an extracted mass spectrum, specifically at a marker compound peak retention time can be used to authenticate a botanical. The method uses at least two-dimensional data at the same time. The ion chromatogram forms one dimension and the mass spectrum forms another dimension. This is different than prior approaches in that the profile property, instead of the marker's properties, are used in the method(s) described herein. For example, in the marker-oriented approach, the marker's chromatographic peak property, such as peak area, peak height, are used in quantitation. In the marker-fingerprint approach described above, not only are the marker's peak property used for authentication, but also the properties other peak(s) that are detected in the same ion chromatogram. In another example, in the marker-oriented approach, the particular marker's ion intension, in MS scan, SIT, or MRM mode, are used for the LC-MS quantitation. In the marker-fingerprint approach described above, not only are the marker's ion intensity used for authentication, but also the profile of the mass spectrum, including the ion intensity of other adduct ions and fragment ions.

The present technology is different from the fingerprint-oriented approach because only the marker(s) related fingerprints are used in the present technology. In the fingerprint-oriented approach, the FT-IR, NMR, or other spectra of the whole sample is used. These spectra of the fingerprint-oriented approach are not specific to a marker compound.

EXEMPLIFICATION

Example 1

Samples

Three authentic NA black cohosh extracts (NA1-3), three Asian black cohosh (*Actaea cimicifuga*) extracts (A1-3), and four commercial black cohosh samples (U1-4) were provided by a collaborator. These extracts were diluted with 70% methanol to about 5 mg/mL. Four standards, cimifugin, cimiracemoside C (cimigenol-3-alpha-L-arabinoside), 27-deoxyactein (23-epi-26-deoxyactein), and actein were purchased from ChromaDex (Irvine, CA). These standards were prepared in 70% methanol at about 5 μg/mL. The standards' structures, CAS Registry numbers, and monoisotopic masses are shown below. Home-made black cohosh samples, M-5 and M-10, were prepared by mixing NA black cohosh sample (NA1) and Asian black cohosh (A1) at 95:5 and 90:10 mass ratios, respectively. Sample solutions were filtered by 0.2 micron PTFE membrane prior to the analysis

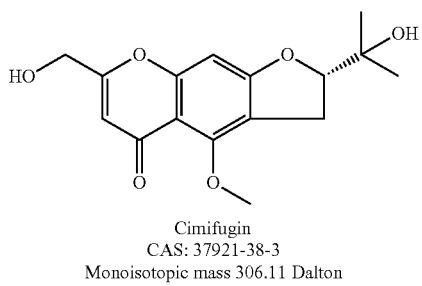

Cimifugin
CAS: 37921-38-3
Monoisotopic mass 306.11 Dalton

-continued

Cimiracemoside C
CAS: 256925-92-5,
Monoisotopic mass: 620.39 Dalton 27-deoxyactein
CAS: 264624-38-6,
monoisotopic mass: 660.39 Dalton Actein
CAS: 18642-44-9
Monoisotopic mass: 676.38 Dalton LC Conditions The liquid chromatography conditions used in this example are shown in Table 1.

TABLE 1

| | LC Conditions |
|---|---|
| System | ACQUITY ® UPLC ® H-Class and QDa ® (with Diverter Valve) |
| Column | ACQUITY ® BEH C18, 2.1 × 100 mm 1.7 micron (p/n 186002352) |
| Column Temp. | 50° C. |
| Eluent A | De-ionized water with 0.1% Formic Acid |
| Eluent B | Acetonitrile/Methanol (v/v 7/3) with 0.1% Formic Acid |
| Injection Volume | 10 μl |
| Run Time | 9 min |
| Reconditioning | 2.5 min |

Table 2 shows the elution gradient for the liquid chromatography system.

TABLE 2

LC Elution Gradient

| Time (Min) | Flow Rate (mL/Min) | % A | % B | Curve |
|---|---|---|---|---|
| Initial | 0.40 | 80 | 20 | Initial |
| 0.5 | 0.40 | 80 | 20 | 6 |
| 4.0 | 0.40 | 35 | 65 | 6 |
| 6.0 | 0.40 | 0 | 100 | 6 |
| 9.0 | 0.40 | 0 | 100 | 6 |
| 9.1 | 0.40 | 80 | 20 | 6 |

The conditions of the detector, a QDa® mass detector, commercially available from Waters Corporation (Milford, MA) are shown in Table 3.

TABLE 3

QDa ® Detector Conditions

| | |
|---|---|
| Software | Empower 3 |
| Detection | ESI+, MS Scan |
| Scan | 200-1000 Da |
| Capillary Voltage | 1.5 kV |
| Cone Voltage | 10 V |
| Probe Temperature | 300° C. |
| Sampling Rate | 5 Hz |
| Diverter valve events | Switch on/Flow to QDa ® detector at 0.8 min., switch off/Flow to waste at 9 min |

Results and Discussion

Quantitative Parameters for Authentication.

Cimiracemoside C was selected as the marker for the authentic black cohosh. The extracted ion chromatograms (XIC) at the marker's molecular ion mass to charge ratio (m/z 621 Dalton) from NA black cohosh samples shared a simple and consistent pattern that was significantly different from the XICs from Asian black cohosh samples (see, FIG. 3). In addition, the mass spectra extracted at the marker's peak retention time (RT) 5.77 min showed a characteristic pattern (see FIG. 4). These patterns, or fingerprints, from two orthogonal dimensions were the bases for this NA black cohosh authentication method.

Figure 3:
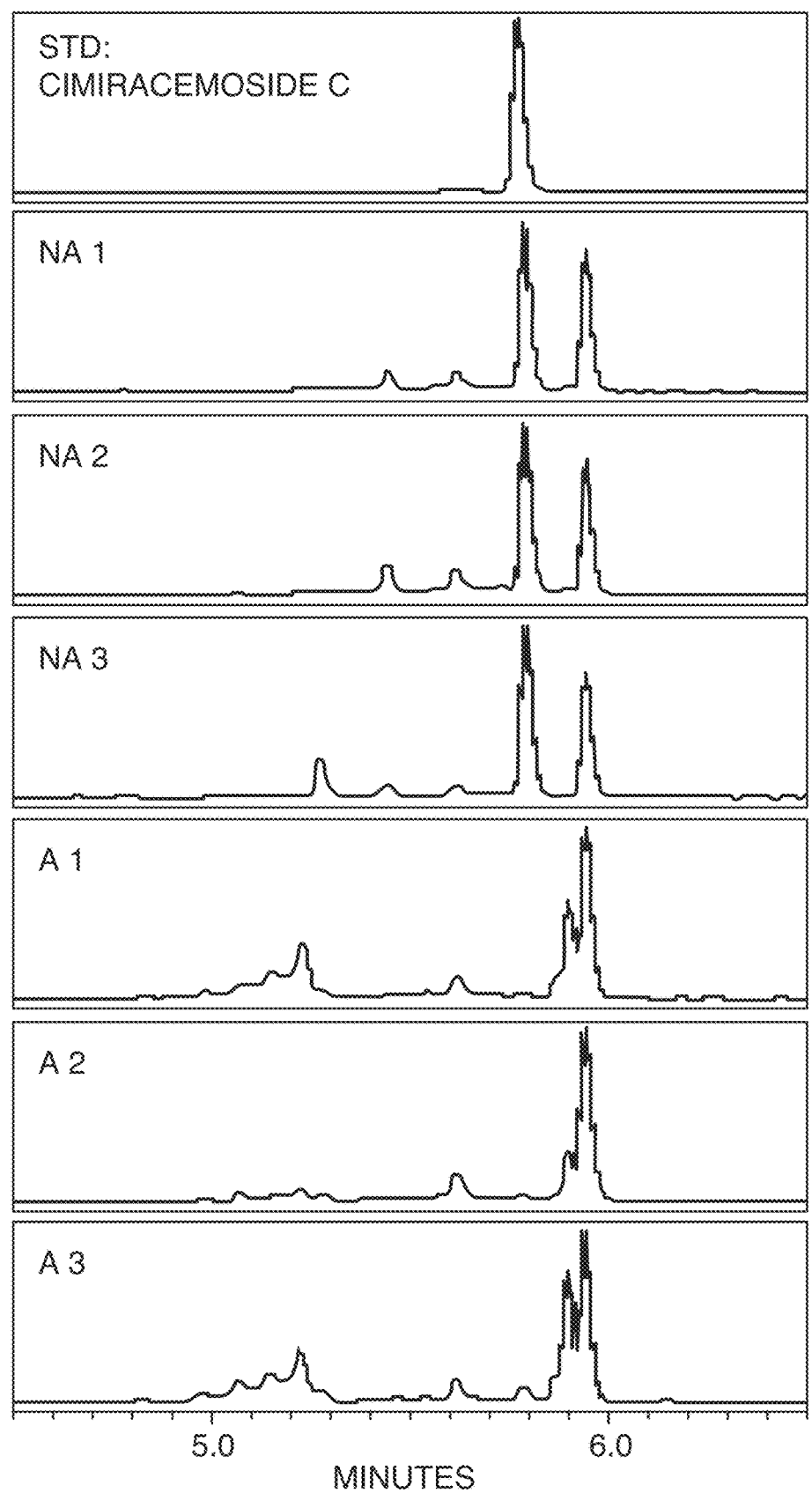
FIG. 3 shows the extracted ion chromatograms of cimiracemoside C (m/z 621 Dalton) in standards, NA black cohosh (NA 1-3), and Asian black cohosh (A 1-3) samples, according to an illustrative embodiment of the technology.

Chromatographic Pattern:

The common feature in the XICs of NA black cohosh was that there were two main peaks of about the equal peak heights, and the marker's peak was one of them (FIG. 3, NA1-3). The marker peak's RT and its peak relative area were used as the quantitative parameters to characterize this chromatographic pattern. Additional parameters can be used, but these two parameters are effective enough to differentiate NA black cohosh from Asian black cohosh samples.

Mass Spectral Pattern:

The top five abundant ions in the extracted mass spectra from NA black cohosh samples were used to characterize the pattern. These ions include the molecular ion (base peak, m/z 621 Da), a fragment ion (m/z 603 Da), the sodium adduct ion (m/z 643 Da), and the isotopic ions (m/z 622, 644 Da). Their m/z and relative intensity (relative to the base peak, or the molecular ion) values were used as the quantitative parameters for authentication. It should be noted that these mass spectra were obtained from the NA black cohosh samples, not from the cimiracemoside C standard. So, it is necessary to include those adduct and isotopic ions, in addition to the molecular ion and the fragment ion, to capture the overall spectral pattern of NA black cohosh samples at the UPLC® chromatography system RT 5.77 min. UPLC® chromatography systems are commercially available from Waters Technologies Corporation (Milford, MA).

Figure 4A:
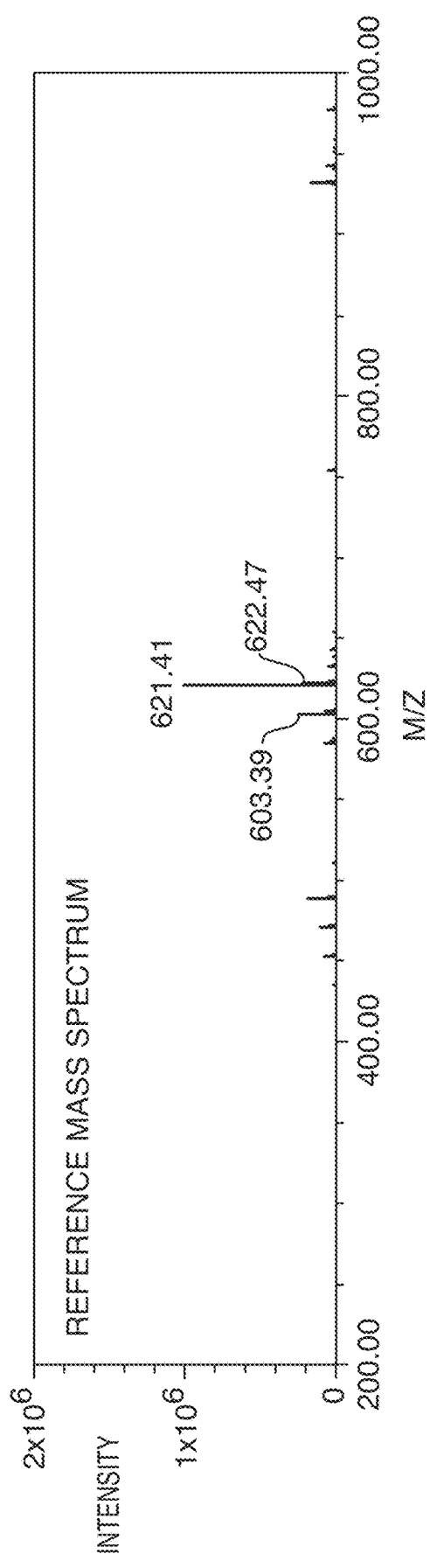
FIG. 4A shows the mass spectrum of the marker (cimiracemoside C) peak in a reference mass spectra in the North American black cohosh MS library (top spectrum), according to an illustrative embodiment of the technology.
Figure 4B:
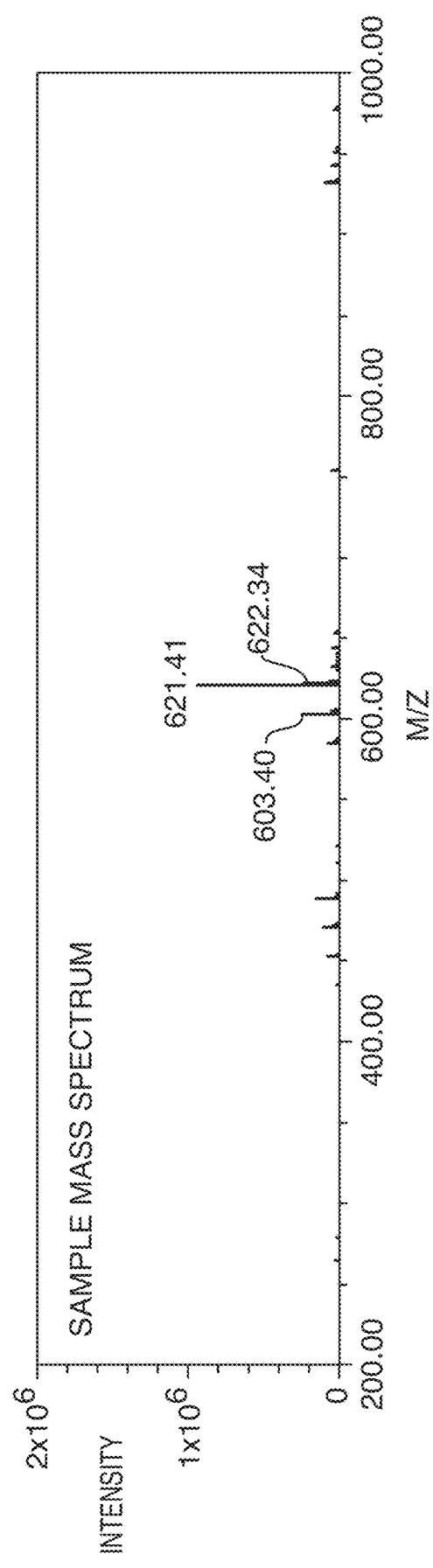
FIG. 4B shows the mass spectrum of the marker (cimiracemoside C) peak in a sample (bottom spectrum) matches one of the reference mass spectra in the North American black cohosh MS library (FIG. 4A), according to an illustrative embodiment of the technology.

MS Library Match:

The extracted mass spectra (at RT 5.77 min) were stored in a custom made NA black cohosh MS library, and were used for MS library search in the unknown black cohosh sample authenticity testing. A screen shot of the MS library match result is shown in FIG. 4.

Threshold Values for Automated Analysis

Figure 5:
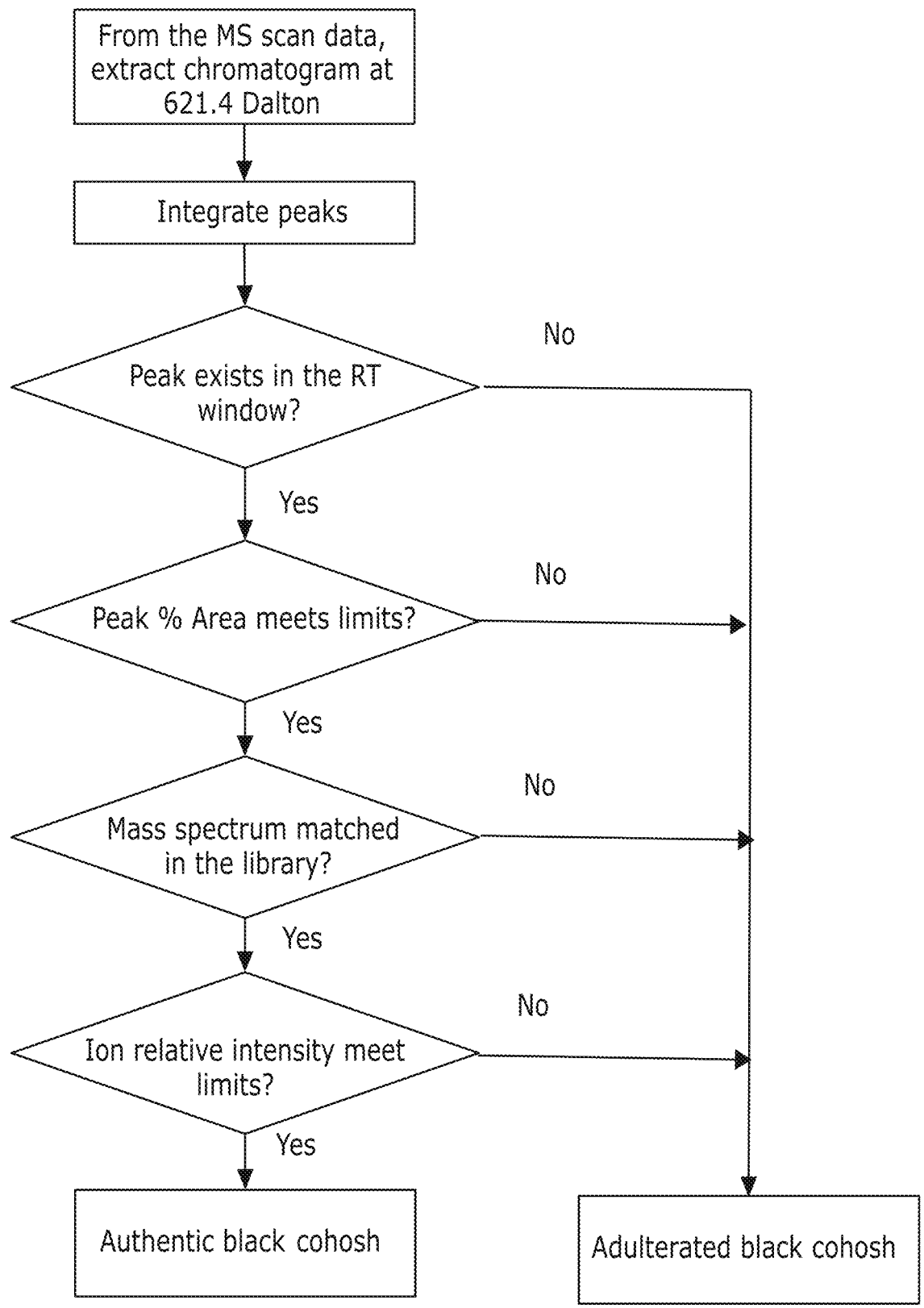
FIG. 5 is a flow chart showing authenticity data process protocol for black cohosh using a single marker's chromatographic pattern and its mass spectral pattern, according to an illustrative embodiment of the technology.

To determine the threshold values in those authentication parameters for the NA black cohosh, three NA black cohosh and three Asian black cohosh samples were measured in triplicate by UPLC®-MS. These samples were measured in a randomized fashion to avoid artifacts related to injection order. Table 4 shows the statistical averages, the standard deviations (SD), and the threshold values for those authentication parameters. In Table 4, the upper and the lower limits in RT were set at the ±1% of the RT average. For the relative peak area (% Area), the limits were set at the 3 times of the SD from the average. For the expected mass relative intensity, the lower limits were set at the 3 times of the SD below the average. There was no upper limit used for the expected mass relative intensity. These threshold values were mainly chosen at the 3 times of the SD to cover the potential wide variation in NA black cohosh. Empower® software commercially available from Waters Corporation (Milford, MA) was used for data processing. A method set was created to carry out the authentication process. FIG. 5 shows the data processing flow chart used by the Empower® software. Table 5 shows the Empower® software functions that were used in the Empower® software method.

TABLE 4

Characteristics of the Chromatographic Pattern and the Mass Spectral Patter
for NA Black Cohosh, and the Threshold Values in Authentication Parameters

| | Ion chromatogram pattern | | Mass spectral pattern | | | | | | | | |
|---|---|---|---|---|---|---|---|---|---|---|---|
| | | | Expected mass 1 | | Expected mass 2 | | Expected mass 3 | | Expected mass 4 | | Expected mass 5 | |
| | | | m/z | Intensity | m/z | Intensity | m/z | Intensity | m/z | Intensity | m/z | Intensity |
| Paramters | RT (min)+ | % Area | (Da) | (%) | (Da) | (%) | (Da) | (%) | (Da) | (%) | (Da) | (%) |
| Average | 5.771 | 50.3 | 621 | 97 | 643 | 75 | 622 | 34 | 644 | 23 | 603 | 18 |
| SD | 0.005 | 3.3 | | 6 | | 22 | | 5 | | 5 | | 3 |

TABLE 4-continued

Characteristics of the Chromatographic Pattern and the Mass Spectral Patter for NA Black Cohosh, and the Threshold Values in Authentication Parameters

| | Ion chromatogram pattern | | Mass spectral pattern | | | | | | | | |
|---|---|---|---|---|---|---|---|---|---|---|---|
| | | | Expected mass 1 | | Expected mass 2 | | Expected mass 3 | | Expected mass 4 | | Expected mass 5 | |
| Paramters | RT (min)+ | % Area | m/z (Da) | Intensity (%) | m/z (Da) | Intensity (%) | m/z (Da) | Intensity (%) | m/z (Da) | Intensity (%) | m/z (Da) | Intensity (%) |
| Upper limit++ | 5.829 | 60 | — | — | — | — | — | — | — | — | — | — |
| Lower limit | 5.713 | 40 | — | 79 | — | 9 | — | 17 | — | 7 | — | 8 |

+±1% of the RT is used for the upper and lower limits
++Upper limits for mass spectral pattern are not used

TABLE 5

The NA Black Cohosh Authentication Criteria and the Related Empower® Software Functions and Fields Used in the Empower® Software data Processing Method Set

| Authentication criteria | Empower functions and fields |
|---|---|
| | Derived channel for XIC at 621.4 Dalton; XIC peak integration. |
| Peak exist in the RT window? | Peak found in the RT window that specified in the Component Table; |
| Peak % Area meets the limits? | % Area within the component suitability limits. |
| Mass spectrum matched in the MS library? | Spectrum found in the Empower MS Library Search; |
| Ion relative intensity meet limits? | MS Expected Masses found, and the Expected Intensities are higher than the limits; |

Analysis of Commercial and Home-Made Black Cohosh Samples

Four commercial black cohosh samples (U1-4) and two home-made black cohosh samples (M-5 and M-10) were tested by this method. FIG. 6 shows a screen shot of an Empower® software report for these samples. Any nonconformity to the authentication criteria was automatically flagged in red color by Empower® software, and is shown with an asterisk (*) in FIG. 6. The authentic, unauthentic, and contaminated black cohosh samples were all correctly determined.

Benefit of Authentication Approach

Chemometric analyses are powerful tools in the exploratory authenticity studies of botanicals. In the routine analysis environment, however, they are too sophisticated and cumbersome to be implemented. Here, a novel authentication approach is demonstrated, in which a marker compound's 2-dimensional fingerprints are used to authenticate NA black cohosh. Because only the marker's chromatographic fingerprint and mass spectral fingerprint are processed, the amount of the data that needs to be processed is relatively small, and the data handling is relatively simple. The whole data processing can be automated in Empower® software commercially available from Waters Corporation, which is suitable for routine analysis labs.

Conclusions

The details of an automated 2-dimensional fingerprint analysis for NA black cohosh authenticity are described. The key features, or patterns, in the chromatographic fingerprints and the mass spectral fingerprints of a marker compound were characterized by a set of quantitative parameters, such as RT, peak relative area, m/z, and ion relative intensity. The threshold values in these parameters for NA black cohosh were determined and used in the automated Empower® software data processing. This UPLC®-MS system method was able to differentiate NA black cohosh from Asian black cohosh samples, and detect Asian black cohosh contamination at 5 wt %. It should be noted that due to the limited number of the reference or training samples used in the method development, this black cohosh authenticity method may need to be further validated.

The features of this UPLC®-MS system approach include the use of a QDa® mass detector, the use of a marker's 2-dimensional fingerprints for authentication and the automation of the whole data processing by Empower® software. The QDa® mass detector is affordable, easy to learn and use. The automated Empower® software data processing is quick and objective. These features are suitable for routine authenticity testing, where the analysis time and analytical expertise may be limited. This new UPLC®-MS system approach can be easily implemented in routine analytical labs for the authentication, or quality control of botanical ingredients and finished products in dietary supplements, herbal medicines, cosmetics and personal care products to safeguard the product quality and safety.

Example 2

The ACQUITY® QDa® mass detector was specially designed to provide chromatographers and non-expert users access to mass data. It presents a practical solution to bringing LC-MS to the routine analysis lab environment. In this example, the feasibility of using a QDa® mass detector for authenticity testing was demonstrated in a study for North American (NA) black cohosh (*Actaea recemosa*). In this example, a method for botanical authentication was developed using the MS data collected by a QDa® mass detector. The accuracy of this authentication method was evaluated in a blind test with four commercial black cohosh samples. The advantages of MS over evaporative light scattering detector (ELSD) were also highlighted.

The samples, LC conditions shown in Table 1, LC elution gradient shown in Table 2, and the detector conditions shown in Table 3 of Example 1 were used in this example. In addition Table 6 shows the ELSD conditions.

TABLE 6

| ELSD Conditions | |
|---|---|
| Gain | 250 |
| Pressue | 45.0 psi |
| Drift Tube Temperature | 55° C. |
| Nebulizer | Heating at 50% power level |

TABLE 6-continued

ELSD Conditions

| Data Rate | 10 pps |
|---|---|
| Filter Time Constant | Normal |

UPLC®-MS System Method Optimization

Figure 7C:
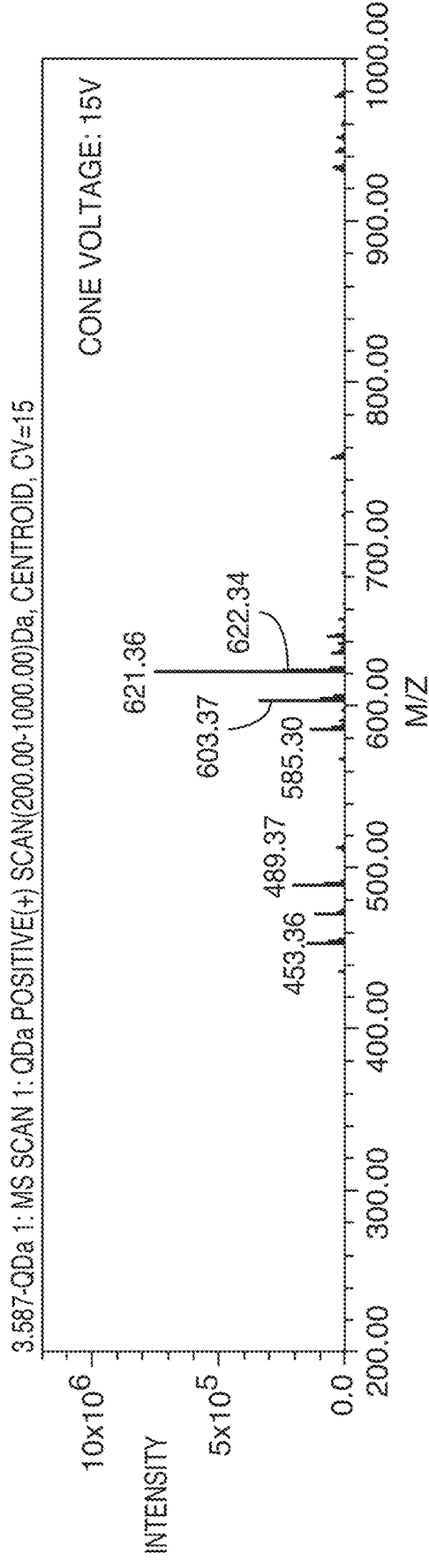
FIG. 7C is a mass spectrum showing the effects of cone voltage (15V) on the cimiracemoside C mass spectrum, according to an illustrative embodiment of the technology. The cone voltages are shown in the sepctra.
Figure 7D:
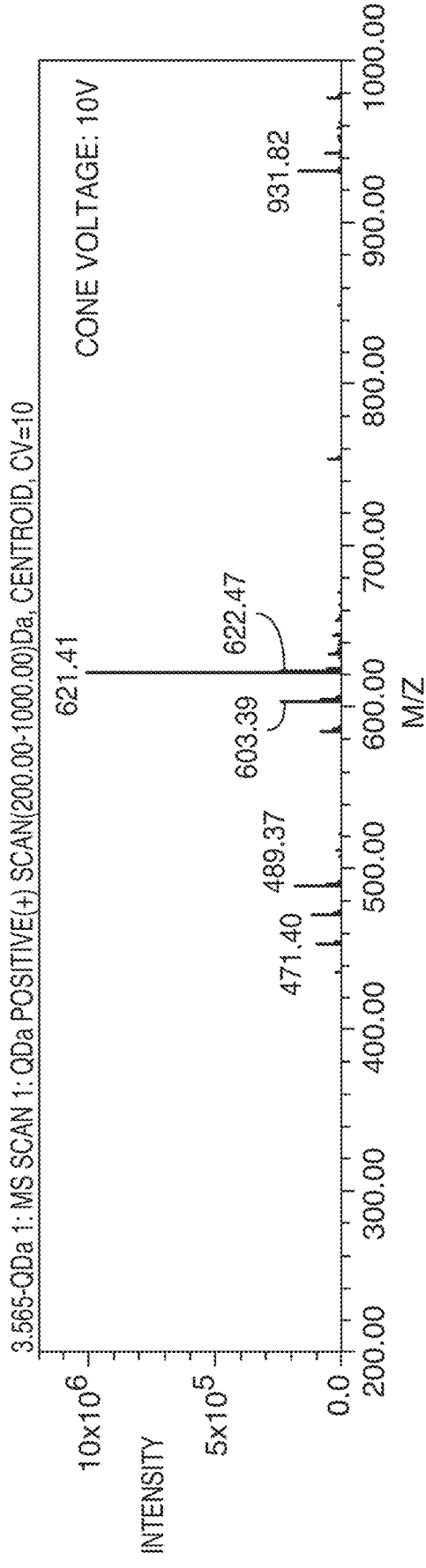
FIG. 7D is a mass spectrum showing the effects of cone voltage (10V) on the cimiracemoside C mass spectrum, according to an illustrative embodiment of the technology. The cone voltages are shown in the sepctra.
Figures 8A, 8B, 8C, 8D:
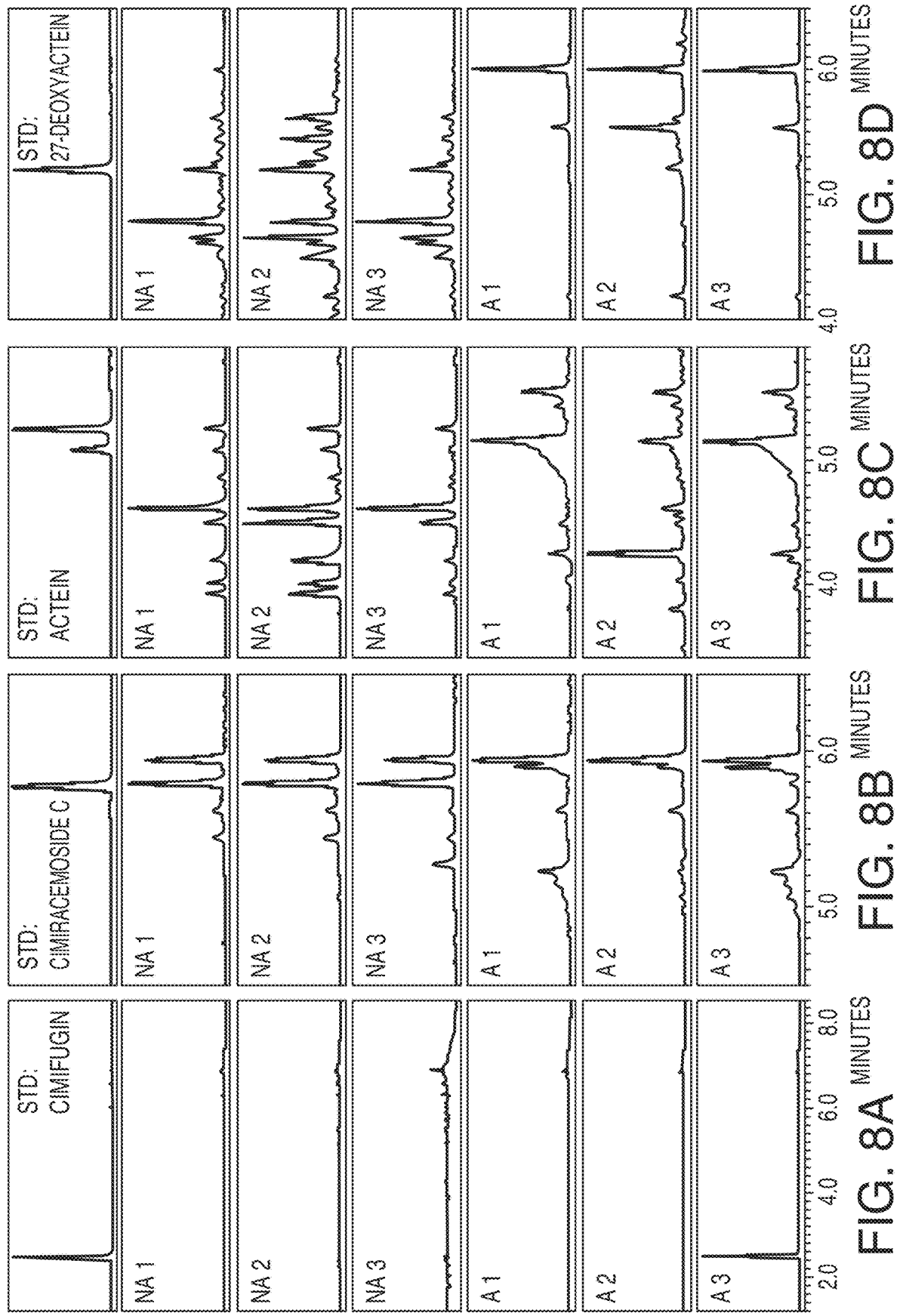
FIG. 8A is an extracted ion chromatograms of cimifugin (307 Dalton) in stands, NA black cohosh (NA 1-3), and Asian black cohosh (A1-3) samples, according to an illustrative embodiment of the technology. For clarity, only the interested XIC sections are shown.
FIG. 8B is an extracted ion chromatograms of cimiracemoside C (621 Dalton) in stands, NA black cohosh (NA 1-3), and Asian black cohosh (A1-3) samples, according to an illustrative embodiment of the technology. For clarity, only the interested XIC sections are shown.
FIG. 8C is an extracted ion chromatograms of actein (659 Dalton) in stands, NA black cohosh (NA 1-3), and Asian black cohosh (A1-3) samples, according to an illustrative embodiment of the technology. For clarity, only the interested XIC sections are shown.
FIG. 8D is an extracted ion chromatograms of 27-deoxyactein (661 Dalton) in stands, NA black cohosh (NA 1-3), and Asian black cohosh (A1-3) samples, according to an illustrative embodiment of the technology. For clarity, only the interested XIC sections are shown.

The QDa® mass detector default setting is suitable for many applications. In this black cohosh study, in order to get the maximum molecular ion intensity, the QDa® detector instrument parameters, such as the probe temperature, the capillary voltage, and the cone voltage on the standards' mass spectra were optimized. FIG. 7 shows the effects of the cone voltage on the cimiracemoside C mass spectrum. The QDa® detector parameters that generated the maximum molecular ion intensity were selected and used.

Selection of Marker for Authentic Black Cohosh

Authentic black cohosh, or NA black cohosh, is manufactured from roots and rhizomes of *Actaea racemosa*. The potential contamination or misidentification of black cohosh plant has been a health concern over the years due to the lack of standardization of production. Adverse events of hepatotoxicity associated with the use of black cohosh products have been reported, and it was suspected that unauthentic black cohosh might contribute to some of the incidents. Contamination or misidentification often occurs with Chinese species of *Actaea* such as *A. heracleifolia*, *A. dahurica*, and *A. cimicifuga*, and NA *Actaea* species growing in the same area as NA black cohosh, such as *A. pachypoda*, *A. rubra*, and *A. podocarpa*. Many chemical constituents of black cohosh have been used as biomarkers for authenticity testing. Among these markers, the most common ones, such as cimifugin, cimiracemoside C, actein, and 27-deoxyactein, were screened in this UPLC®-MS system study for suitable marker(s) to be use with the QDa® detector (see FIGS. 8A-8D).

The molecular ions ([M+H]$^+$) of cimifugin, cimiracemoside C, and 27-deoxyactein, and the dehydration ions ([M+H−H$_2$O]$^+$) of actein were the dominant ions (base peak) in their respective mass spectra (data not shown). The mass to charge ratios (m/z) of these base peak ions were used to extract the ion chromatograms from the MS scan data, respectively. And the resulting extracted ion chromatograms (XICs) are shown in FIGS. 8A-8D. After inspection of the XICs in FIGS. 8A-8D, the cimiracemoside C (m/z 621 Da, retention time 5.8 min in FIG. 8B) was selected as the marker for NA black cohosh because it showed the most simple and distinctive chromatographic pattern in the NA black cohosh as compared to the pattern from the Asian black cohosh.

Authenticity Data Processing Protocol

In order to make the authenticity method suitable for routine analysis, a new authenticity data processing protocol was designed. This protocol uses the marker's distinctive chromatographic and mass spectral patterns, or fingerprints, to evaluate the sample authenticity (FIG. 5). This authenticity data processing protocol was implemented in Empower® 3 software program using MS library match and other existing functions. No special chemometric software program was used. Details of how this protocol was developed and implemented in Empower® 3 software are discussed in Example 1.

To support this authenticity data processing protocol, a black cohosh MS library was created in Empower® software. The cimiracemoside C mass spectra from NA black cohosh samples were extracted (with baseline subtraction) from the MS scan data, and stored in this custom-made NA black cohosh MS library. Empower® software MS library match function was used to check if sample's mass spectrum matched to any of the reference mass spectra in the library. The Empower® 3 software MS library can be custom built, exported and imported. FIG. 4 shows a MS library match result. UV/Vis spectra can also be used for authenticity testing. However, UV/Vis spectra are usually less specific when compared to mass spectra. In this case, the cimiracemoside C is UV transparent. So, it is not useful to use the UV/Vis spectral library for the black cohosh authenticity testing.

Analysis of Commercial and Home-Made Black Cohosh Samples

Four commercial black cohosh samples (U1-4) and two home-made black cohosh samples (M-5 and M-10) were tested by this method. The commercial samples' origins were revealed after the evaluation was completed. Table 7 is a summary of the authenticity test results for these samples. The authentic NA black cohosh (U2 and U3) and the un-authentic black cohosh (U1 and U4) samples were correctly determined. The contaminated samples were also correctly detected, including the 5 wt % contaminated black cohosh sample (M-5).

TABLE 7

Black Cohosh Sample Authenticity Test Results and the Samples' Origins

| Sample | Marker peak in RT window detected? | Marker peak relative Area within threshold? | MS library match found? | Expected ion relative abundance within threshold? | Authentic black cohosh? | Sample Origin |
|---|---|---|---|---|---|---|
| U 1 | + | − | + | − | No | *Actaea Cimicifuga* |
| U 2 | + | + | + | + | Yes | *Actaea racemosa* |
| U 3 | + | + | + | + | Yes | *Actaea racemosa* |
| U 4 | + | − | + | − | No | *Actaea dahurica* |
| M-5 | + | + | + | − | No | Contamination at 5 wt % |
| M-10 | + | + | + | − | No | Contamination at 10 wt % |

Comparison of MS and ELSD for Authenticity Testing

Figure 9A:
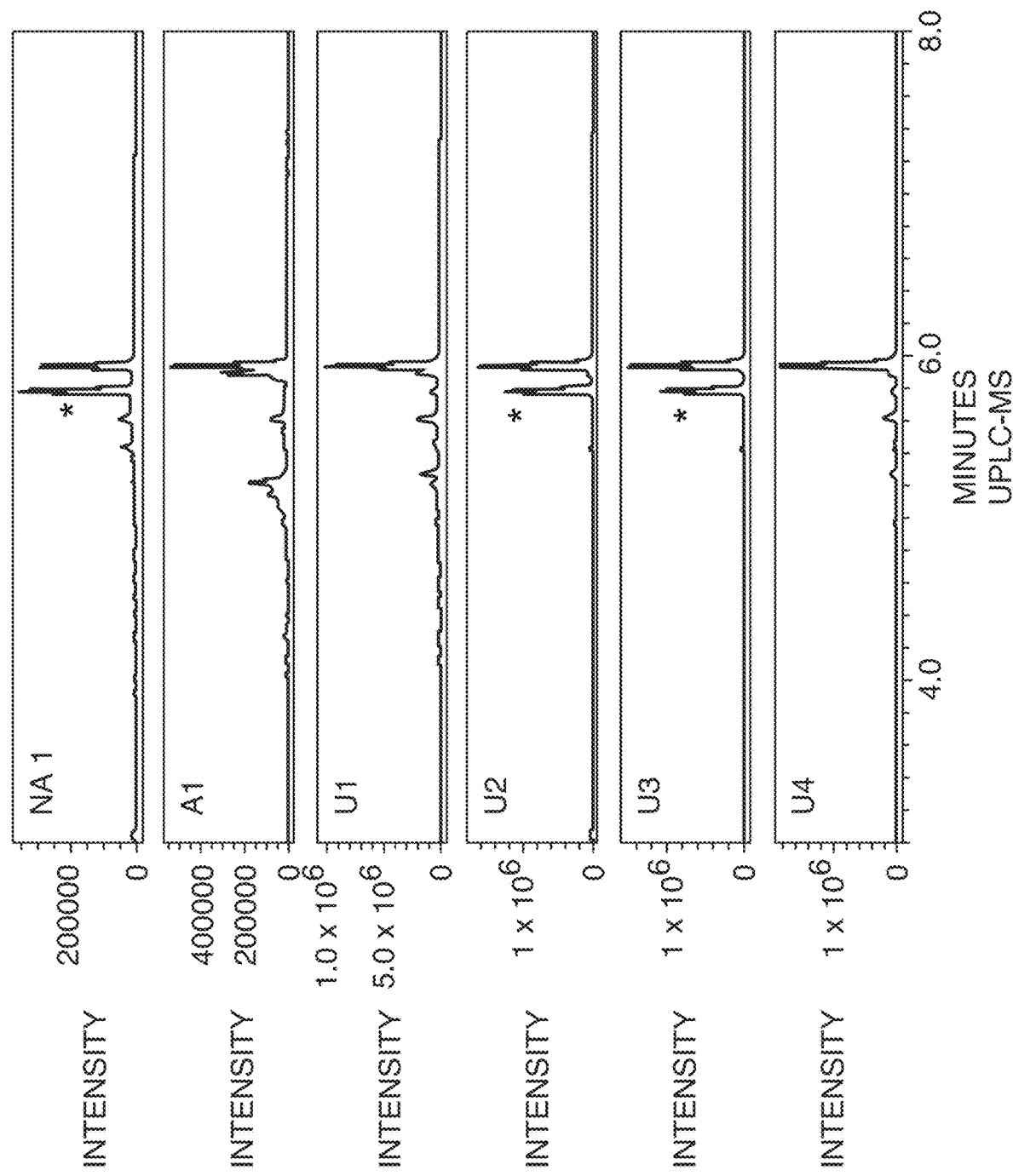
FIG. 9A are chromatograms showing UPLC®-MS XICs chromatograms for a NA black cohosh (NA1), an Asian black cohosh (A 1), and four unknown black cohosh samples (U 1-4), according to an illustrative embodiment of the technology. The marker peak in FIG. 9A is labeled by an asterisk (*). The UPLC®-MS XICs are extracted at 621 Dalton. The UPLC® conditions are the same for all chromatograms. UPLC®-MS system is commercially available from Waters Technologies Corporation (Milford, MA).
Figure 9B:
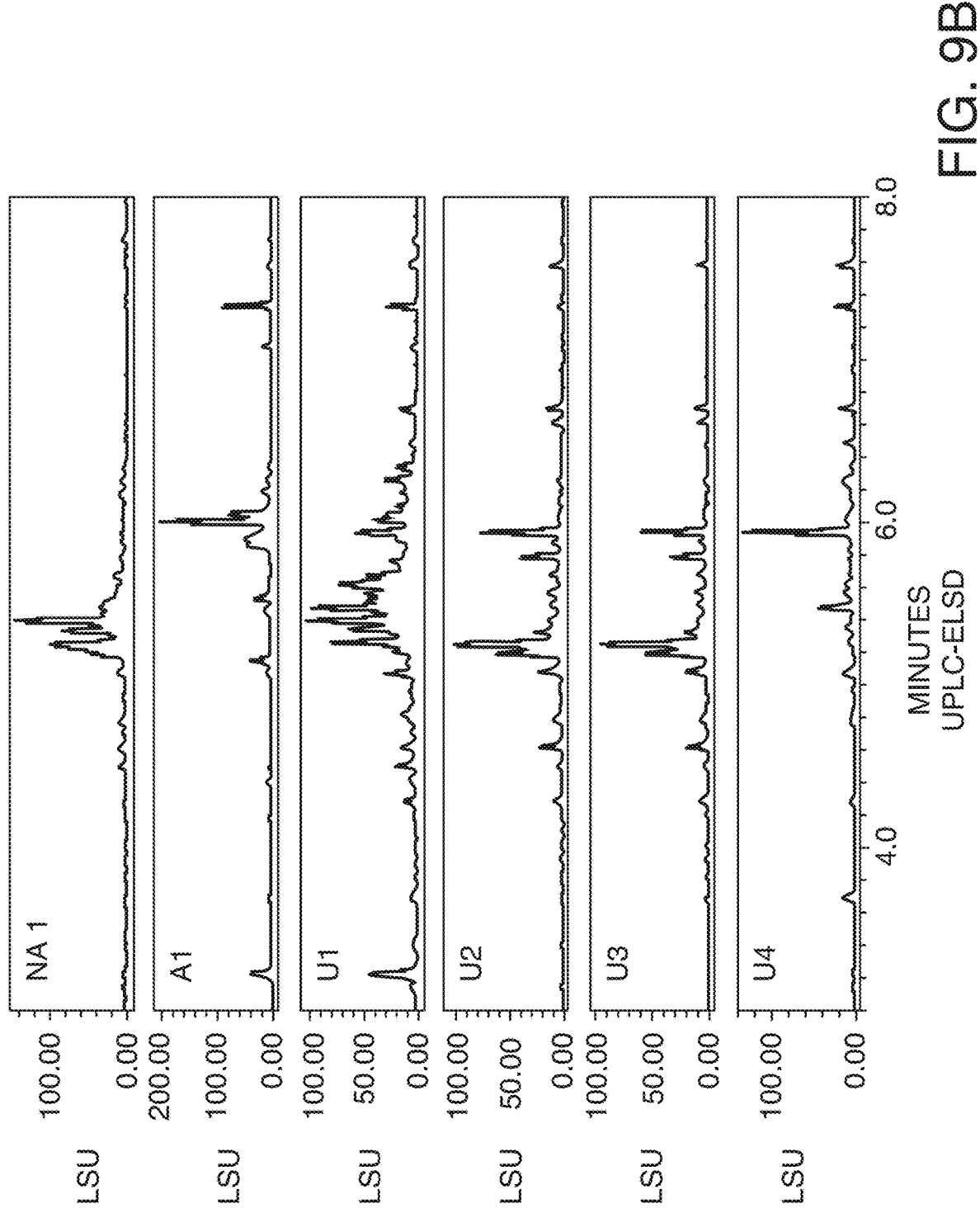
FIG. 9B are chromatograms showing a UPLC®-ELSD chromatograms for a NA black cohosh (NA1), an Asian black cohosh (A 1), and four unknown black cohosh samples (U 1-4), which can be compared to the UPLC®-MS XICs of FIG. 9A, according to an illustrative embodiment of the technology. UPLC®-ELSD system is commercially available from Waters Technologies Corporation (Milford, MA).

Evaporative light scattering detector (ELSD) is commonly used for the black cohosh identification. A comparison of the MS and the ELSD for the authenticity testing was made with a NA black cohosh (NA 1), an Asian black cohosh (A 1), and 4 unknown black cohosh samples (see FIGS. 9A and 9B). The LC conditions were the same for these chromatograms. From the UPLC®-MS chromatograms (FIG. 9A), it is easy to tell that the samples U2 and U3 are authentic black cohosh, and samples U1 and U4 are not. On the contrary, it is difficult to tell from the ELSD chromatograms (FIG. 9B) which unknown sample is authentic black cohosh. FIGS. 9A and 9B shows clearly that MS is a better technique in differentiating complex botanic samples than the ELSD.

Conclusions

In this Example, a method for black cohosh authentication was developed using an ACQUITY® UPLC® H-Class system (available from Waters Technologies Corporation, Milford MA) and a QDa® mass detector (also available from Waters Technologies Corporation, Milford MA). Specifically, four black cohosh constituents, cimifugin, cimiracemoside C, 27-dexoyactein, and actein were screened, and the cimiracemoside C was selected as the marker. A new automated data processing approach that is suitable for routine authenticity testing was used. In this data processing protocol, the marker's chromatographic and mass spectral data were evaluated. This authenticity method was tested with four commercial black cohosh samples and two homemade contaminated NA black cohosh samples. All authentic and un-authentic or contaminated samples were correctly identified. It should be noted that due to the limited number of the training or reference samples used in the method development, this black cohosh authenticity method may need further validation.

This Example demonstrates that the QDa® mass detector is well fitted to botanical authentication, which is an essential test for product safety and quality. The cimiracemoside C ion chromatogram collected by a QDa® mass detector had less interfering peaks, and showed clear difference between the NA and Asian black cohosh samples. The cimiracemoside C mass spectrum contained characteristic mass spectral pattern that was used for authenticity testing. The QDa® mass detector is simple to use and affordable, and can be widely implemented in routine analytical labs for the botanical authentication. The adoption of QDa® mass detector in authenticity testing can greatly improve the speed and confidence in the botanical authentication, and help to ensure safe and high quality dietary supplements, herbal medicines, cosmetics and personal care products on the market.

The invention claimed is:

1. A method for authenticating a botanical comprising:
identifying at least one marker compound of the botanical;
injecting a sample comprising the botanical into a chromatography system comprising a mobile phase delivery module, an autosampler, a chromatography column, a chromatography column manager, and a data acquisition module in communication with at least one detector comprising a mass spectrometer, wherein the data acquisition module is a computer having software installed to collect and analyze data received from the detector;
extracting a chromatogram of the at least one marker compound, the extracted chromatogram comprising at least one peak;
extracting a mass spectrum at a chromatographic peak retention time of the at least one marker compound, the extracted spectrum comprising at least one band;
integrating the at least one peak of the extracted chromatogram to determine a marker compound peak relative area using the data acquisition module;
quantifying the at least one peak of the extracted chromatogram;
quantifying the at least one band of the extracted mass spectrum;
comparing the quantified at least one peak of the extracted chromatogram to an authentic sample chromatogram and the quantified at least one band of the extracted mass spectrum to an authentic sample mass spectrum at the same time wherein the sample is authenticated by an authentication protocol comprising determining (a) whether the at least one peak of the extracted chromatogram is detected within a peak retention window of an at least one peak of the authentic sample chromatogram, (b) whether the marker compound peak relative area is within threshold limits of a marker compound peak relative area of the authentic sample mass spectrum, (c) whether the mass spectrum is matched in a spectrum library, and (d) whether an ion relative abundance of the at least one band of the extracted mass spectrum is within threshold limits of an ion relative abundance of the authentic mass spectrum, wherein the software automates the authenticity data process protocol, and wherein the botanical is authenticated when all values of the quantified at least one peak and the quantified at least one band are within the predetermined standard deviation or percentage threshold value and the extracted mass spectrum matches the predetermined mass spectrum.

2. The method of claim 1, wherein the botanical comprises a plant extract, a plant powder, a plant tincture, an herbal medicine, or a botanical ingredient for cosmetic and personal care products.

3. The method of claim 1, wherein the sample comprising the botanical has a consistent concentration of about 5 mg/ml.

4. The method of claim 1, wherein the chromatogram is extracted at a mass to charge ratio of an ion that is characteristic to the at least one marker compound.

5. The method of claim 1, wherein the at least one detector further comprises a UV-Visual spectrophotometer or a photodiode array detector.

6. The method of claim 5, wherein the chromatogram is extracted at a UV-Vis wavelength that is characteristic to the at least one marker compound.

7. The method of claim 1, wherein the at least one detector further comprises a Fourier-transform infrared spectrometer.

8. The method of claim 7, wherein the chromatogram is extracted at an IR wavenumber that is characteristic to the at least one marker compound.

9. The method of claim 1, wherein the at least one detector further comprises a nuclear magnetic resonance spectrometer.

10. The method of claim 9, wherein the chromatogram is extracted at an NMR chemical shift that is characteristic to the at least one marker compound.

11. The method of claim 1, wherein the extracted mass spectrum is extracted at an apex of the at least one peak.

12. The method of claim 1, wherein integrating the at least one peak of the extracted chromatogram comprises detecting a start point and an end point of a baseline of the at least one peak, calculating areas and heights of the at least one peak, and finding apex retention times of the least one peak.

13. The method of claim 1, wherein quantifying peaks on the extracted chromatogram comprises calculating a relative peak area of the at least one peak, relative to the sum of the peak areas of all the detected peaks on the extracted chromatogram.

14. The method of claim 1, further comprising identifying a mass to charge ratio of an ion that is characteristic to the at least one marker compound, and calculating an intensity of the at least one band.

15. The method of claim 5, further comprising identifying a maximum absorption wavelength and calculating an intensity of the at least one band.

16. The method of claim 7, further comprising identifying a maximum absorption wavenumber and calculating an intensity of the at least one band.

17. The method of claim 9, further comprising identifying a chemical shift of spectral peaks and calculating an intensity of the at least one band.

18. The method of claim 14, wherein the intensity is a relative ion peak abundance of a most intensive ion peak in the extracted mass spectrum.

\* \* \* \* \*